United States Patent
Schwartz et al.

(12)

(10) Patent No.: US 6,495,721 B1
(45) Date of Patent: Dec. 17, 2002

(54) SERTRALINE HYDROCHLORIDE FORM II AND METHODS FOR THE PREPARATION THEREOF

(75) Inventors: Eduard Schwartz, Rechovot; Tamar Nidam, Yehud; Anita Liberman, Tel-Aviv; Marioara Mendelovici, Rechovot; Judith Aronhime, Rehovot, all of (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 09/575,634

(22) Filed: May 22, 2000

Related U.S. Application Data

(63) Continuation-in-part of application No. 09/448,985, filed on Nov. 24, 1999.
(60) Provisional application No. 60/182,159, filed on Feb. 14, 2000, and provisional application No. 60/147,888, filed on Aug. 9, 1999.

(51) Int. Cl.[7] ............................................. C07C 211/42
(52) U.S. Cl. ...................................................... 564/308
(58) Field of Search ........................................... 564/308

(56) References Cited

U.S. PATENT DOCUMENTS

| 4,536,518 A | 8/1985 | Welch, Jr. et al. |
| 5,082,970 A | 1/1992 | Braish |
| 5,248,699 A | 9/1993 | Sysko et al. |
| 5,463,126 A | 10/1995 | Williams |
| 5,734,083 A | 3/1998 | Wilson et al. |

FOREIGN PATENT DOCUMENTS

| JP | 2000-26378 | 1/2000 |
| JP | 2000-26379 | 1/2000 |
| WO | 99/47486 | 9/1999 |

OTHER PUBLICATIONS

Willard M. Welch et al. "Nontricyclic Antidepressant Agents Deirved from cis– and trans–1–Amino–4–aryltetralins", 1984 Journal of Medicinal Chemistry, vol. 27, No. 11; pp 1508–1515.

*Primary Examiner*—Samuel Barts
(74) *Attorney, Agent, or Firm*—Kenyon & Kenyon

(57) ABSTRACT

The present invention is directed to Form II of sertraline hydrochloride and novel methods for its preparation. According to the present invention, sertraline hydrochloride Form II may be produced directly form sertraline base or sertraline mandelate. It may also be produced from sertraline hydrochloride solvate and hydrate forms, and crystallized from new solvent systems. Pharmaceutical compositions containing sertraline hydrochloride Form II and methods of treatment using such pharmaceutical compositions are also disclosed.

22 Claims, 3 Drawing Sheets

SERTRALINE HYDROCHLORIDE FORM II AND METHODS FOR THE PREPARATION THEREOF

CROSS-REFERENCE TO RELATED APPLICATIONS

This application claims the benefit of provisional application Serial No. 60/182,159, filed Feb. 14, 2000, and is a continuation-in-part of application Ser. No. 09/448,985, filed Nov. 24, 1999, which claims the benefit of provisional application No. 60/147,888, filed Aug. 9, 1999. The contents of each of these applications are incorporated herein by reference.

FIELD OF THE INVENTION

The present invention relates to a novel crystalline form of sertraline hydrochloride, and reproducible methods for its preparation.

BACKGROUND OF THE INVENTION

Sertraline hydrochloride, (1S-cis)-4-(3,4dichlorophenyl)-1,2,3,4-tetrahydro-N-methyl-1-naphthalenamine hydrochloride, having the formula

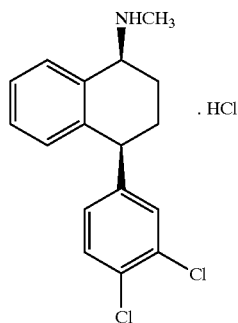

is approved, under the trademark Zoloft®, by the U.S. Food and Drug Administration, for the treatment of depression, obsessive-compulsive disorder and panic disorder.

U.S. Pat. No. 4,536,518 ("the '518 patent") describes the preparation of sertraline hydrochloride with a melting point of 243–245° C. by treating an ethyl acetate/ether solution of the free base with gaseous hydrogen chloride. The solid state properties of the sertraline hydrochloride so produced are not otherwise disclosed.

U.S. Pat. No. 5,734,083 describes the preparation of a form of sertraline hydrochloride denominated polymorph "T1."

According to U.S. Pat. No. 5,248,699 ("the '699 patent"), the sertraline hydrochloride produced by the method of the '518 patent has a crystalline form denominated "Form II." The '699 patent discloses four other polymorphs of sertraline hydrochloride designated Forms I, III, IV, and V, and characterizes them by single crystal x-ray analysis, powder x-ray diffraction, infra-red spectroscopy, and differential scanning calorimetry. The '699 patent reports that Form II is produced by rapid crystallization of sertraline hydrochloride from an organic solvent, including isopropyl alcohol, ethyl acetate or hexane, and generally describes methods for making sertraline hydrochloride Forms I–V. According to this patent, the preferential formation of Forms I, II or IV in an acidic solution consisting of isopropyl alcohol, hexane, acetone, methyl isobutyl ketone, glacial acetic acid or, preferably, ethyl acetate, depends on the rapidity of crystallization. The only method described in this patent for making Forms II and IV is by the rapid crystallization of sertraline hydrochloride from an organic solvent such as those listed above.

The experimental procedure for the preparation of sertraline hydrochloride described in the '518 patent, was repeated in the laboratory. According to the '699 patent, the '518 procedure produces sertraline hydrochloride Form II. Four experiments were performed according to the description in the '518 patent. By following the procedures described in the '699 patent for preparation of sertraline hydrochloride Form II, we were unable to obtain sertraline hydrochloride Form II. Thus there remains a need for reproducible methods for the preparation of sertraline hydrochloride Form II.

SUMMARY OF THE INVENTION

The present invention relates to a process for making sertraline hydrochloride Form II comprising the steps of dissolving sertraline base or sertraline mandelate in an organic solvent to form a solution; adding hydrogen chloride to the solution; heating the solution to a temperature between about room temperature and about reflux for a time sufficient to induce the formation of sertraline hydrochloride Form II; and isolating sertraline hydrochloride Form II.

The present invention also relates to a process for making sertraline hydrochloride Form II comprising the steps of dissolving sertraline hydrochloride in dimethylformamide, cyclohexanol, acetone or a mixture thereof; heating the solution for a time sufficient to effect transformation to sertraline hydrochloride Form II; and isolating sertraline hydrochloride Form II.

The present invention further relates to a process for making sertraline hydrochloride Form II comprising the steps of granulating sertraline hydrochloride Form V in ethanol or methanol; and stirring the mixture of sertraline hydrochloride Form V and ethanol or methanol for a time sufficient to induce transformation to sertraline hydrochloride Form II.

The present invention still further relates to a process for making a mixture of sertraline hydrochloride Form II and Form V comprising the steps of heating sertraline hydrochloride ethanolate Form VI at up to 1 atmosphere pressure; and isolating a mixture of sertraline hydrochloride Form II and Form V.

The present invention still further relates to a process for making sertraline hydrochloride Form II comprising the steps of suspending a water or solvent adduct of sertraline hydrochloride in a solvent selected from the group consisting of acetone, t-butyl-methyl ether, cyclohexane, n-butanol, and ethyl acetate such that a slurry is formed, for a time sufficient to effect transformation to sertraline hydrochloride Form II; and filtering the slurry to isolate sertraline hydrochloride Form II.

The present invention still further relates to sertraline hydrochloride Form II, characterized by an x-ray powder diffraction pattern comprising peaks at about 5.5, 11.0, 12.5, 13.2, 14.7, 16.4, 17.3, 18.1, 19.1, 20.5, 21.9, 22.8, 23.8, 24.5, 25.9, 27.5, and 28.0 degrees two theta; pharmaceutical compositions for the treatment of depression comprising sertraline hydrochloride Form II together with a pharmaceutically acceptable carrier, and a method for treating depression comprising the step of administering to a subject in need of such treatment a therapeutically effective amount of the such a pharmaceutical composition.

DETAILED DESCRIPTION OF THE INVENTION

Form II from Sertraline Base or Sertraline Mandelate

The present invention provides new processes for making sertraline hydrochloride Form II from sertraline base or sertraline mandelate. Sertraline base may be made by methods known in the art, including the methods of the '518 patent. Sertraline base is dissolved in a suitable solvent. Suitable solvents include ethyl acetate, acetone, t-methyl-butyl ether, isopropyl alcohol, n-butanol, t-butanol, isobutanol, hexane, and cyclohexane, and mixtures thereof The pH of the sertraline base solution is lowered by the addition of hydrogen chloride, which may result in a temperature increase. As used herein, "hydrogen chloride" includes both gaseous hydrogen chloride and aqueous hydrogen chloride (i.e. hydrochloric acid). Hydrogen chloride also may be added as a solution with an organic solvent, such as a solution of isopropyl alcohol and hydrogen chloride, n-butanol and hydrogen chloride, acetone and hydrogen chloride, or the like. The solution of sertraline base or sertraline mandelate in the solvent is heated to a temperature between about room temperature and the reflux temperature of the solvent and maintained at that temperature for a period of time sufficient to effect the transformation to sertraline hydrochloride Form II. Preferably the solution is heated to a temperature between about 45° C. and the reflux temperature of the solvent. Most preferably the solution is heated to at or about the reflux temperature of the solvent. Upon cooling of the mixture, for example to room temperature, sertraline hydrochloride Form II is isolated by filtration.

In a preferred variation of this method, the solution of sertraline base or sertraline mandelate in a solvent is heated to the reflux temperature of the solvent. The mixture is refluxed for a time sufficient to effect the transformation to sertraline hydrochloride Form II. Preferably the mixture is refluxed for about 1 to 4 hours.

Numerous experiments were performed in an attempt to repeat the procedure described in U.S. Pat. No. 4,536,518 for preparing Form II wherein sertraline base was dissolved in ethyl acetate, ether was added and the solution was acidified with gaseous hydrogen chloride. The material obtained after filtration and air drying was sertraline hydrochloride amorphous, not Form II as was expected. These experiments are set forth in Examples 13–16 below.

Figure 1:
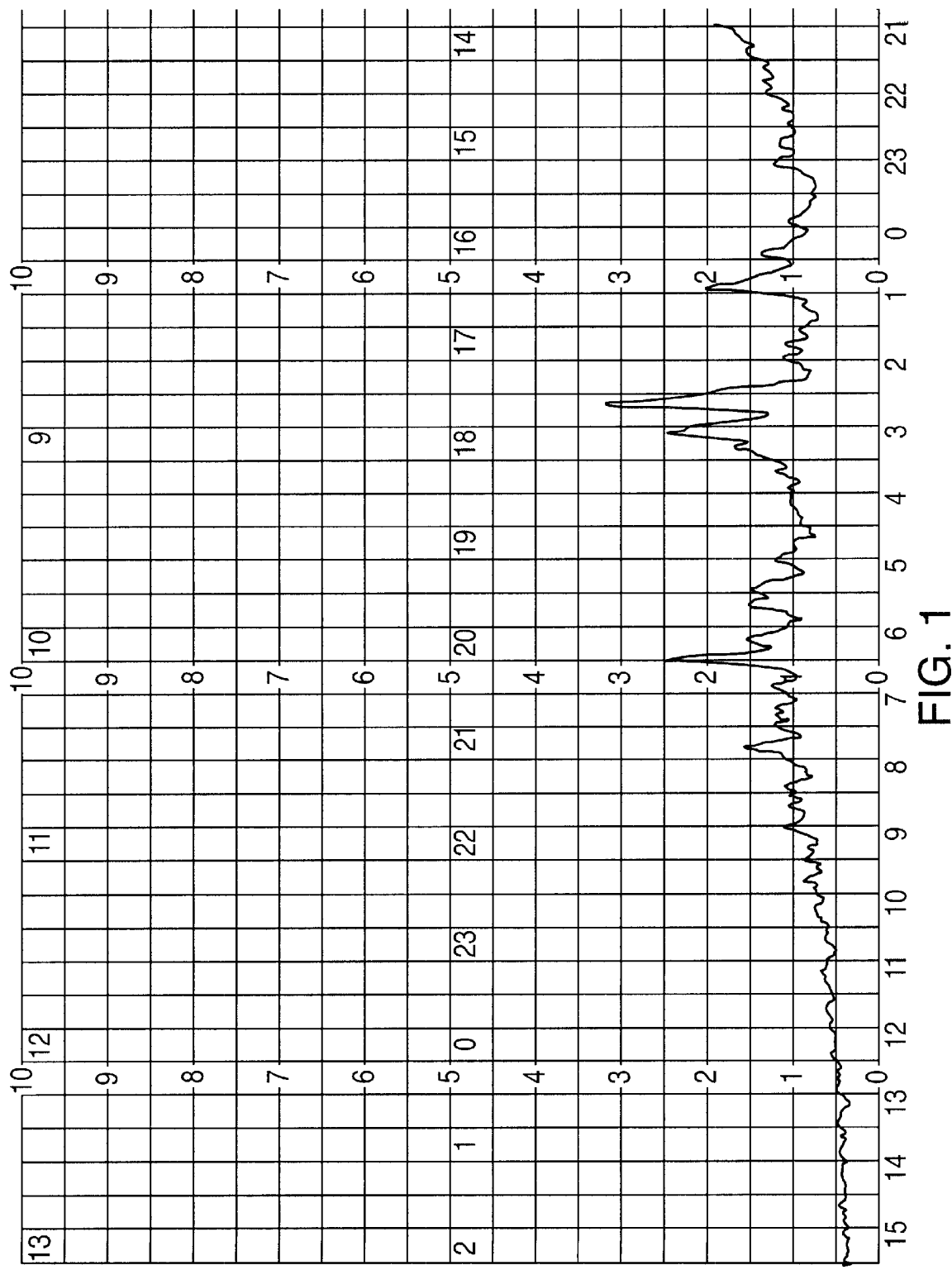
FIG. 1 is a characteristic x-ray powder diffraction spectrum of sertraline hydrochloride prepared by the methods of U.S. Pat. No. 4,536,518.

The x-ray powder diffraction graphs for the products of each of these experiments are equivalent, containing peaks at 11.0, 12.0, 15.4, 16.2, 22.4, 22.9 degree two-theta (See FIG. 1 for a representative example). FIG. 1 does not contain the typical peaks of sertraline hydrochloride Form II, indicating an absence of sertraline hydrochloride Form II in those samples. Thus, none of these experiments, which follow the procedure described in the '518 patent for preparation of sertraline hydrochloride Form II, leads to sertraline hydrochloride Form II.

The '699 patent provides experimental procedures for preparation of sertraline hydrochloride. The '699 patent does not provide experimental procedure for preparation of sertraline hydrochloride Form II, but it is mentioned that sertraline hydrochloride Form II may be prepared by "rapid crystallization" from the same solvents.

Figure 2:
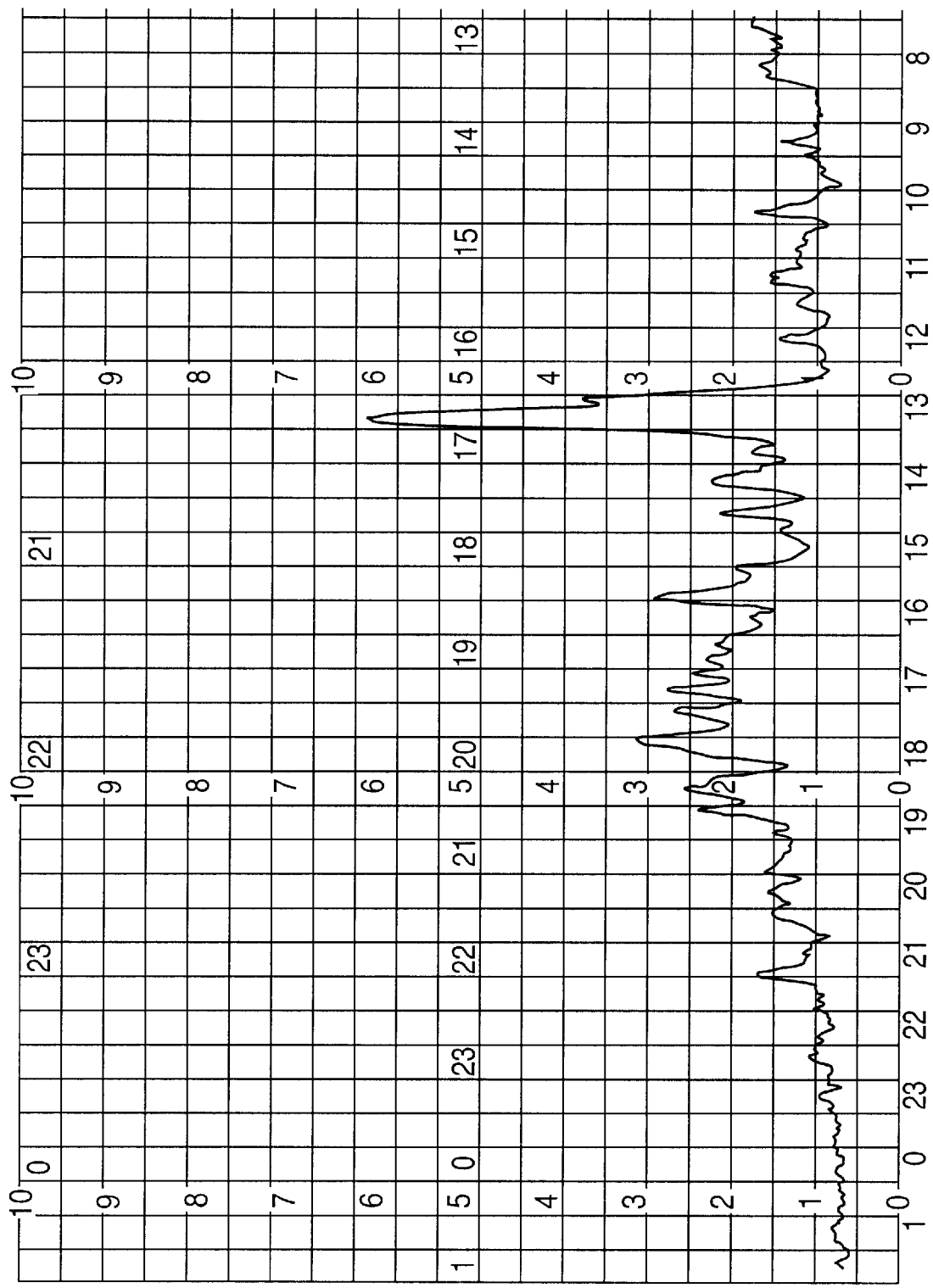
FIG. 2 is a characteristic x-ray powder diffraction spectrum of sertraline hydrochloride prepared by the methods of U.S. Pat. No. 5,248,699.

The procedure of the '699 patent was repeated in an attempt to prepare sertraline hydrochloride form 11 from ethyl acetate. In a trial of the methods according to the '699 patent: An aqueous solution of sodium hydroxide, 10%, was added to a slurry of sertraline mandelate crystals (44.6 g) in ethyl acetate (290 mL), until complete dissolution. The organic phase was separated and the aqueous phase was extracted with ethyl acetate (280 mL) and combined with the organic phase. The resulting organic solution was washed with water (5×100 mL) then with brine (100 mL) and concentrated on a rotavapor to a volume of 356 mL. The concentrated solution was cooled to 58° C. and seeded with sertraline hydrochloride Form II. Concentrated hydrochloric acid (32%, 8.1 mL) was added to this solution. The solution was then rapidly cooled to 30° C. over 5 minutes. A heavy gel was obtained and the stirring was continued overnight. The solid was filtrated, washed with ethyl acetate and dried at 50° C. The dried solid, sertraline hydrochloride, was not sertraline hydrochloride Form II, as shown by the x-ray diffraction pattern of FIG. 2.

By following the procedures described in the '699 patent for preparation of sertraline hydrochloride Form II, we did not obtain sertraline hydrochloride Form II. It is thus apparent that neither the '699 patent nor the '518 patent disclose a useful method for the preparation of sertraline hydrochloride Form II.

Form II from Sertraline Hydrochloride

The present invention also provides new processes for making sertraline hydrochloride Form II from sertraline hydrochloride Form V by granulation. In the conversion of sertraline hydrochloride Form V to sertraline hydrochloride Form II, sertraline hydrochloride Form V is combined with a small amount of ethanol or methanol. The mixture of sertraline hydrochloride Form V and ethanol or methanol is stirred for at least a period of at least a few hours, up to several days, preferably about two days, to induce the transformation of Form V to Form II. Sertraline hydrochloride Form II is then isolated by filtration.

The present invention also provides new processes for making sertraline hydrochloride Form II by recrystallization of sertraline hydrochloride under heating conditions. In the conversion of sertraline hydrochloride to sertraline hydrochloride Form II, sertraline hydrochloride is dissolved in a suitable organic solvent. The solution is then heated for a time sufficient to effect transformation to sertraline hydrochloride Form II. Suitable solvents include dimethylformamide, cyclohexanol and acetone. Dimethylformamide is preferred. The suspension may be heated to a temperature between about 70° C. and 120° C. Sertraline hydrochloride Form II is then isolated by filtration.

The present invention provides new processes for making sertraline hydrochloride Form II from sertraline hydrochloride Form VI, Form VII or Form VIII by reslurry in organic solvents at temperatures between 25–80° C., followed by drying. Sertraline hydrochloride Form VI may be made following the methods of Examples 2 and 3. Sertraline hydrochloride Form VII is a water adduct and may be made by the methods of Examples 19 and 20. Sertraline hydrochloride Form VIII may be made by the methods of Examples 17 and 18. The methods provided in the present invention have advantages over the rapid recrystallization method of U.S. Pat. No. 5,248,699. The method of the present invention does not require complete dissolution of sertraline hydrochloride, controlling the rate of heating or cooling of a sertraline solution, or controlling the rate of crystallization. The present method utilizes less solvent than the method of the '699 patent, since the sertraline hydrochloride starting material need not be completely dissolved.

In the conversion of sertraline hydrochloride Form VI, Form VII or Form VIII to sertraline hydrochloride Form II, according to the present invention, sertraline hydrochloride Form VI, Form VII water adduct, or Form VIII is combined with an aprotic organic solvent to form a slurry. Suitable solvents include n-butanol, acetone, t-butyl-methyl ether (MTBE), ethyl acetate and cyclohexane. The conversion may take place at room temperature, but preferably the sertraline hydrochloride Form VI, Form VII water adduct, or VIII and solvent are heated to temperatures between 25° C. and 80° C. About 1 to about 10 volumes of solvent are preferred, based on the weight of the sertraline hydrochloride starting material. See Examples 8 (3 volumes of solvent) and 9 (5 volumes of solvent) below. Smaller amounts of solvent will also effect the transformation, albeit in some instances more slowly. The reaction is carried out for a time sufficient to convert the Form VI, Form VII or Form VIII to Form VI. We have not observed any further conversion of Form II upon treatment under these conditions for times longer than the minimum time necessary to effect the transformation.

The present invention also provides new processes for making a mixture of sertraline hydrochloride Form II and sertraline hydrochloride Form V. In this embodiment of the present invention, sertraline hydrochloride Form VI is heated to induce the transformation of sertraline hydrochloride Form VI to a mixture of both sertraline hydrochloride Form II and sertraline hydrochloride Form V. In this embodiment of the present invention, the heating of sertraline hydrochloride Form VI may be done under reduced pressure or atmospheric pressure.

Pharmaceutical Compositions Containing Sertraline Hydrochloride Polymorphs

In accordance with the present invention, sertraline hydrochloride Form II as prepared by the new methods disclosed herein may be used in pharmaceutical compositions that are particularly useful for the treatment of depression, obesity, chemical dependencies or addictions, premature ejaculation, obsessive-compulsive disorder and panic disorder. Such compositions comprise at least one of the new crystalline forms of sertraline hydrochloride with pharmaceutically acceptable carriers and/or excipients known to one of skill in the art.

For example, these compositions may be prepared as medicaments to be administered orally, parenterally, rectally, transdermally, bucally, or nasally. Suitable forms for oral administration include tablets, compressed or coated pills, dragees, sachets, hard or gelatin capsules, sub-lingual tablets, syrups and suspensions. Suitable forms of parenteral administration include an aqueous or non-aqueous solution or emulsion, while for rectal administration suitable forms for administration include suppositories with hydrophilic or hydrophobic vehicle. For topical administration the invention provides suitable transdermal delivery systems known in the art, and for nasal delivery there are provided suitable aerosol delivery systems known in the art.

Suitable non-toxic pharmaceutically acceptable carriers and/or excipients will be apparent to those skilled in the art of pharmaceutical formulation, and are discussed in detail in the tet entitled *Remington's Pharmaceutical Science*, $17^{th}$ edition (1985), the contents of which are incorporated herein by reference. Obviously, the choice of suitable carriers will depend on the exact nature of the particular dosage form, e.g. for a liquid dosage form, whether the composition is to be formulated into a solution, suspension, gel, etc, or for a solid dosage form, whether the composition is to be formulated into a tablet, capsule, caplet or other solid form, and whether the dosage form is to be an immediate- or controlled-release product.

Experimental Details

The powder X-ray diffraction patterns were obtained by methods known in the art using a Philips X-ray powder diffractometer, Goniometer model 1050/70 at a scanning speed of 2° per minute, with a Cu radiation of $\lambda=1.5418$ Å

EXAMPLES

The present invention will now be further explained in the following examples. However, the present invention should not be construed as limited thereby. One of ordinary skill in the art will understand how to vary the exemplified preparations to obtain the desired results.

Example 1

Preparation of Sertraline Base

Sertraline mandelate was prepared according to procedures in U.S. Pat. No. 5,248,699. Sertraline mandelate (5 g) was stirred at room temperature with 50 mL ethyl acetate. Aqueous sodium hydroxide was added dropwise until the sertraline mandelate was completely neutralized. The phases were separated and the organic phase was dried over $MgSO_4$ and filtered. The solvent was removed under reduced pressure resulting sertraline base as an oil (3.2 g).

Example 2

Preparation of Sertraline Hydrochloride Ethanolate Form VI by Reslurry of Form I Sertraline hydrochloride Form I (1 g) and absolute ethanol (20 mL) were stirred at room temperature for 24 hours. Filtration of the mixture yielded sertraline hydrochloride ethanolate Form VI.

Example 3

Preparation of Sertraline Hydrochloride Ethanolate Form VI by Reslurry of Form V Sertraline hydrochloride Form V (1 g) and ethanol absolute (20 mL) were stirred at room temperature for 24 hrs. Filtration of the mixture yielded sertraline hydrochloride ethanolate Form VI.

Example 4

Preparation of Sertraline Hydrochloride Form II

Sertraline base (3 g) was dissolved in acetone (10 mL). Isopropanol containing hydrogen chloride (20 mL) was added to the solution until the pH is ~2. The stirring was continued overnight at room temperature. The resulting solid was filtered, washed with acetone and dried to yield sertraline hydrochloride Form II (2.61 g, yield 77.6%).

Example 5

Preparation of Sertraline Hydrochloride Form II in n-Butanol

Figure 3:
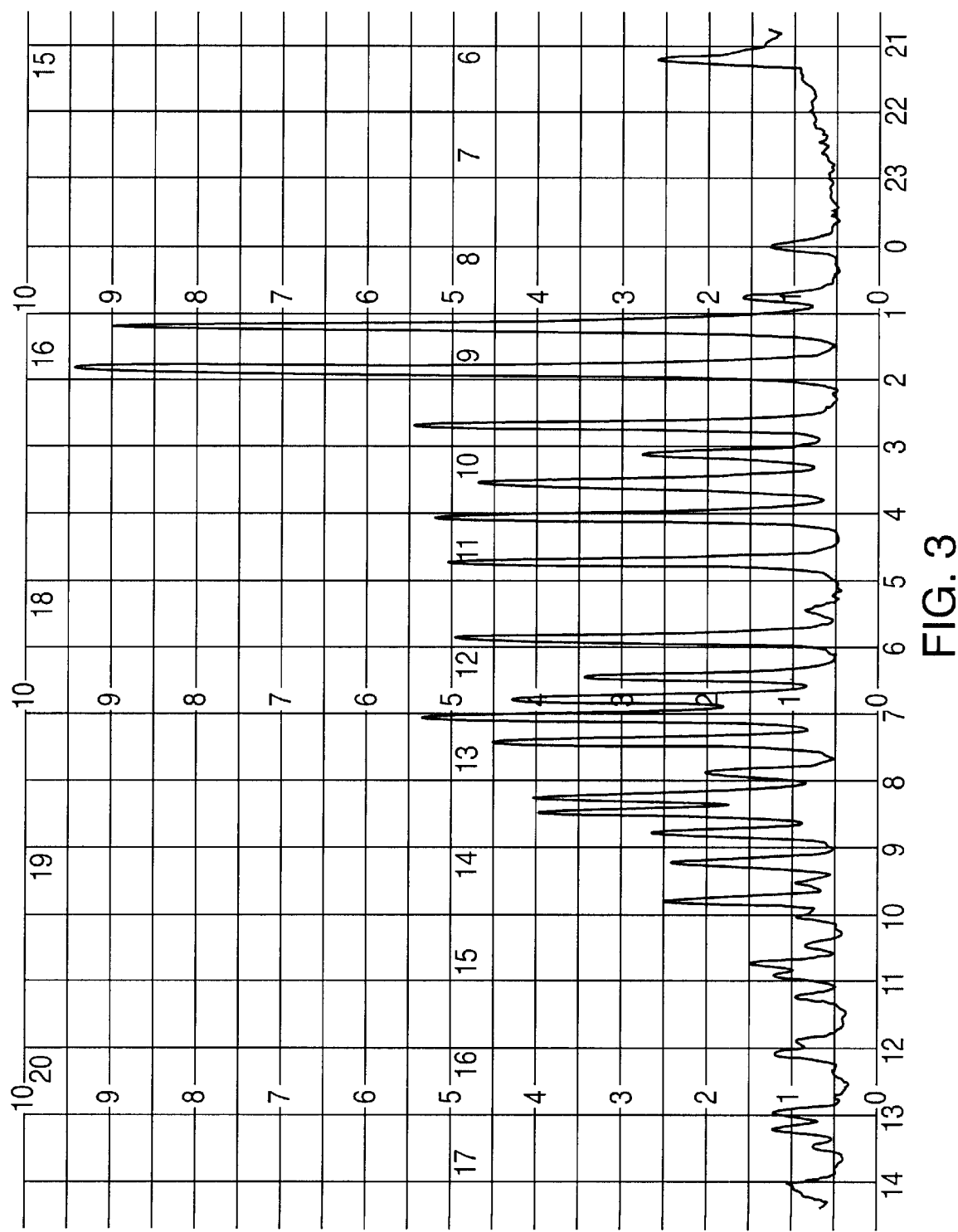
FIG. 3 is a characteristic x-ray powder diffraction spectrum of sertraline hydrochloride Form II prepared by the methods of the present invention.

HCl (g) was bubbled through a solution of sertraline base (33 g) in n-butanol (264 mL). The temperature rose to about 45° C. A gel-like solid was formed. The addition of HCl (g) was continued until pH 0.5 was reached. Then the stirring was continued at room temperature for 2.5 h. During the stirring the solid became a fine crystalline solid. The solid was filtered, washed with n-butanol (2×10 mL) and dried at 80° C. for 24 h. The product is sertraline hydrochloride Form II. The x-ray powder diffraction spectrum obtained is FIG. 3.

Example 6

Preparation of Sertraline Hydrochloride Form II

Sertraline hydrochloride Form V (10 g) was suspended in dimethylformamide (DMF) (30 mL). Heating was started and at about 70° C. a clear solution is obtained. The solution was cooled to room temperature and the solid was filtered. After drying at 80° C. for 24 hrs., sertraline hydrochloride Form II was obtained (6.6 g, yield 66%).

Example 7

Preparation of Sertraline Hydrochloride Form II by Granulation of Form V

Sertraline hydrochloride Form V (2 g) and absolute ethanol (0.5 mL) were stirred in a rotavapor at room temperature for 2 days. At the end of two days, the material contained sertraline hydrochloride Form II.

Example 8

Preparation of Sertraline Hydrochloride Form II from Form VI

A slurry of sertraline hydrochloride Form VI (50 g) and t-butyl-methyl ether (150 mL) were heated to reflux and the reflux was continued for 1 hour. The slurry was then allowed to cool to room temperature and filtered. The solid was washed with t-butyl-methyl ether (50 mL) and dried in a reactor under vacuum of 30 mm Hg with stirring. The dried solid so obtained is sertraline hydrochloride Form II (38.26 g: yield 86.7%).

Example 9

Preparation of Sertraline Hydrochloride Form II from Form VI

Sertraline hydrochloride Form VI (25 g) was stirred with acetone (250 mL) at room temperature for 2 hours. The solid material was filtered and washed twice with acetone (25 mL). The wet solid was dried in a vacuum agitated drier to afford sertraline hydrochloride Form II (20.09 g: yield 98.6%).

Example 10

Preparation of Sertraline Hydrochloride Form II and Sertraline Hydrochloride Form V by Drying Form VI Sertraline hydrochloride ethanolate Form VI was dried at 105° C. under vacuum (<10 mm Hg) over 24 hours. The resulting dried material was sertraline hydrochloride Form II mixed with sertraline hydrochloride Form V.

Example 11

Preparation of Sertraline Hydrochloride Form II from Sertraline Mandelate in n-Butanol Sertraline mandelate (20 g) and n-butanol were stirred at room temperature. The mixture was acidified with hydrogen chloride until pH 0 was reached. During the acidification the temperature of the reaction mixture rose to ~50° C. After the natural cooling to room temperature, the mixture was stirred at room temperature for two hours. The solid was filtrated, washed with n-butanol and dried at 80° C. to afford sertraline hydrochloride Form II (9.02 g).

Example 12

Preparation of Sertraline Hydrochloride Form I from Sertraline Hydrochloride Form VIII Sertraline hydrochloride Form VIII (13 g) was heated in acetone (130 mL) at reflux for 1 hour. The slurry was than cooled to room temperature and the solid was filtrated and washed with acetone (2×10 mL). After drying sertraline hydrochloride Form II was obtained (7.9 g).

Example 13

An aqueous sodium hydroxide solution, 10%, was added drop-wise to a slurry of sertraline mandelate crystals (10 g) in ethyl acetate (650 mL), until complete dissolution was obtained (25 mL). After separation of the phases, the organic phase was washed with water (300 mL) and then dried with $MgSO_4$. The organic solution was diluted with ether (690 mL) and gaseous hydrochloric acid was bubbled through the solution until pH 1.3 was reached. The addition of hydrogen chloride resulted in a temperature increase to about 30° C. The resulting slurry of sertraline was stirred at room temperature overnight. The solid was then isolated by filtration, washed twice with ether (2×20 mL) and air dried. The dried solid, sertraline hydrochloride, was not sertraline hydrochloride Form II, as shown in FIG. 1.

Example 14

An aqueous sodium hydroxide solution, 10%, was added drop-wise to a slurry of sertraline mandelate crystals (15 g) in ethyl acetate (810 mL), until complete dissolution was obtained (35 mL). The organic and aqueous phases were separated and, the organic phase was dried over $MgSO_4$ The organic solution was then diluted with ether (820 mL) and gaseous hydrogen chloride (2.36 g, 2 eq.) was bubbled through the solution until pH 1.5 was reached. The temperature was about 25° C. The slurry was stirred at room temperature overnight. The solid was filtrated, washed with ether (2×15 mL) and air-dried. The dried solid, sertraline hydrochloride, was not sertraline hydrochloride Form II.

Example 15

An aqueous sodium hydroxide solution, 10%, was added drop-wise to a slurry of sertraline mandelate crystals (15 g) in ethyl acetate (810 mL), until complete dissolution was obtained. The organic and aqueous phases were separated and the organic phase was dried over $MgSO_4$ and diluted with an equal volume of ether (820 mL). Gaseous hydrochloric acid (4.82 g) was bubbled through the solution until pH 1 was reached. The slurry was stirred at room temperature overnight. The solid was filtrated, washed with ether (2×15 mL) and air-dried. The dried solid, sertraline hydrochloride, was not sertraline hydrochloride Form II.

Example 16

An aqueous sodium hydroxide solution, 10%, was added drop-wise to a slurry of sertraline mandelate crystals (15 g) in ethyl acetate (810 mL), until complete dissolution is obtained. The phases were separated and the organic phase was dried over $MgSO_4$ and diluted with an equal volume of ether (820 mL). Gaseous hydrogen chloride was slowly bubbled through the solution (over about 3 hours) until pH 1.5 was reached. The slurry was stirred at room temperature over night. The dried solid, sertraline hydrochloride, was not sertraline hydrochloride Form II.

Example 17

Preparation of Sertraline Hydrochloride Form VIII

Sertraline base (2.7 g) was suspended in 27 mL of water. This mixture was heated to 80° C. and treated with hydrochloric acid until about pH 1 was reached. A clear solution was obtained which on cooling gave a precipitate. After 2 hours stirring at room temperature the solid was isolated by filtration. This solid was characterized by powder x-ray diffraction and found to be sertraline hydrochloride Form VIII.

Example 18

Preparation of Sertraline Hydrochloride Form VIII

Sertraline hydrochloride ethanolate (Form VI) (40 g) was stirred with water (80 mL) for 1 hour at room temperature. The slurry was filtrated and washed with water to yield sertraline hydrochloride hydrate Form VIII.

Example 19

Preparation of Sertraline Hydrochloride Form VII

Sertraline hydrochloride Form V (1.003 g) was stirred for 24 hours at room temperature in 20 mL water (HPLC grade). At the end of the stirring the mixture looked like a jelly suspension. The suspension was filtrated and the compound obtained was kept at cold conditions (4° C.) until analyzed by x-ray diffraction.

Example 20

Preparation of Sertraline Hydrochloride Form VII from Form VI

A solution of sertraline hydrochloride ethanolate (Form VI) (40 g) in water (400 mL) was heated at 80° C. and complete dissolution of sertraline hydrochloride ethanolate (Form VI) was obtained. The pH was adjusted to about 1 and the solution was allowed to cool to room temperature and then stirred for 2 additional hours. The solid was isolated by filtration and washed with water to yield sertraline hydrochloride Form VII.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

What is claimed is:

1. A process for making sertraline hydrochloride Form II comprising the steps of:
   (a) dissolving sertraline base or sertraline mandelate in an organic solvent to form a solution;
   (b) adding hydrogen chloride to the solution;
   (c) heating the solution to a temperature between about room temperature and about reflux for a time sufficient to induce the formation of sertraline hydrochloride Form II; and
   (d) isolating sertraline hydrochloride Form II.

2. The process of claim 1 wherein the solvent is selected form the group consisting of ethyl acetate, acetone, hexane, t-butyl-methyl ether, isopropyl alcohol, n-butanol, t-butanol, iso-butanol, and cyclohexane, and mixtures thereof.

3. The process of claim 2 wherein the preferred solvent is t-butyl-methyl ether.

4. The process of claim 2 wherein the preferred solvent is n-butanol.

5. The process of claim 1 wherein the hydrogen chloride is added as gaseous hydrogen chloride.

6. The process of claim 1 wherein the hydrogen chloride is added as a solution of hydrogen chloride.

7. The process of claim 6 wherein the solution of hydrogen chloride is selected from the group consisting of isopropyl alcohol and hydrogen chloride, acetone and hydrogen chloride, and n-butanol and hydrogen chloride.

8. The process of claim 1 wherein the solution is heated to the reflux temperature of the solvent.

9. A process for making sertraline hydrochloride Form II comprising the steps of:
   (a) dissolving sertraline hydrochloride in a solvent selected from the group consisting of dimethylformamide, cyclohexanol, acetone and mixtures thereof;
   (b) heating the solution for a time sufficient to effect transformation to sertraline hydrochloride Form II; and
   (c) isolating sertraline hydrochloride Form II.

10. A process for making sertraline hydrochloride Form II comprising the steps of:
    (a) granulating sertraline hydrochloride Form V in ethanol or methanol; and
    (b) stirring the mixture of sertraline hydrochloride Form V and ethanol or methanol for a time sufficient to induce transformation to sertraline hydrochloride Form II.

11. A process for making sertraline hydrochloride Form II comprising the steps of:
    (a) suspending a water or solvent adduct of sertraline hydrochloride in a solvent selected from the group consisting of acetone, t-butyl-methyl ether, cyclohexane, n-butanol, and ethyl acetate, such that a slurry is formed, for a time sufficient to effect transformation to sertraline hydrochloride Form II; and
    (b) filtering the slurry to isolate sertraline hydrochloride Form II.

12. The process of claim 11 wherein the process takes place at a temperature between about 25° C. and about 120° C.

13. The process of claim 11 wherein the process takes place under reflux conditions.

14. The process of claim 11 in which the sertraline hydrochloride is suspended in about 1 to about 10 volumes of organic solvent.

15. The process of claim 11 wherein the solvent is t-butyl-methyl-ether.

16. The process of claim 11 wherein the solvent is acetone.

17. The process of claim 11 wherein the solvent is ethyl acetate.

18. The process of claim 11 wherein the solvent is n-butanol.

19. The process of claim 11 wherein the sertraline hydrochloride water or solvate adduct is sertraline hydrochloride Form VI.

20. The process of claim 11 wherein the sertraline hydrochloride water or solvate adduct is sertraline hydrochloride Form VII.

21. The process of claim 11 wherein the sertraline hydrochloride water or solvate adduct is sertraline hydrochloride Form VIII.

22. A process for making a mixture of sertraline hydrochloride Form II and Form V comprising the steps of:
    (a) heating sertraline hydrochloride ethanolate Form VI at up to 1 atmosphere pressure; and
    (b) isolating a mixture of sertraline hydrochloride Form II and Form V.

* * * * *